(12) United States Patent
Takahashi et al.

(10) Patent No.: US 7,507,738 B2
(45) Date of Patent: Mar. 24, 2009

(54) 5-PROTECTED AMINOPYRIMIDINE COMPOUND, PRODUCTION METHOD THEREOF AND INTERMEDIATE THEREFOR

(75) Inventors: Daisuke Takahashi, Kawasaki (JP); Kunisuke Izawa, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 525 days.

(21) Appl. No.: 11/081,616

(22) Filed: Mar. 17, 2005

(65) Prior Publication Data

US 2005/0209257 A1 Sep. 22, 2005

(30) Foreign Application Priority Data

Mar. 17, 2004 (JP) ............... 2004-077265

(51) Int. Cl.
- *A01N 43/54* (2006.01)
- *A61K 31/505* (2006.01)
- *C07D 239/42* (2006.01)
- *C07D 401/04* (2006.01)
- *C07D 239/02* (2006.01)

(52) U.S. Cl. ............... 514/256; 514/272; 544/297; 544/319; 544/320

(58) Field of Classification Search ............... 514/256, 514/272; 544/297, 319, 320

See application file for complete search history.

(56) References Cited

U.S. PATENT DOCUMENTS

| | | | |
|---|---|---|---|
| 4,511,718 | A | 4/1985 | Ribaldone et al. |
| 6,380,206 | B1 | 4/2002 | Pamukcu et al. |
| 2004/0230053 | A1 | 11/2004 | Takahashi et al. |
| 2005/0137404 | A1 | 6/2005 | Takahashi et al. |
| 2005/0165234 | A1 | 7/2005 | Takahashi et al. |
| 2005/0176966 | A1 | 8/2005 | Takahashi et al. |
| 2005/0209257 | A1 | 9/2005 | Takahashi et al. |
| 2005/0215789 | A1 | 9/2005 | Takahashi et al. |

FOREIGN PATENT DOCUMENTS

| | | |
|---|---|---|
| EP | 0 647 639 A1 | 4/1995 |
| WO | WO 02/42280 A2 | 5/2002 |
| WO | WO 03/106434 A1 | 12/2003 |

OTHER PUBLICATIONS

E. de la Cuesta, et al., Synthesis of 2-Substituted 4-Oxo-5-nitropyrimidines from Methyl 3-Ethoxy-2-nitroacrylate and Other Reactions, J. Heterocyclic Chem., 22, 337 (1985).*

U.S. Appl. No. 11/417,233, filed May 4, 2006, Takahashi, et al.

Database Crossfire Beilstein, Beilstein Institut zur Foerderung der Wissenschaften, Frankfurt am Main, DE; XP-002336605, Database Accession No. 5470570, Abstract Only.

H.J.G. Broxterman, et al., "Synthesis of Serine Analogues to be Used as Modified Phospho Acceptor Sites in Substrates of Protein Kinase C", Reel. Trav. Chim., Pays-Bas, vol. 110, 1991, pp. 46-52, XP-009050698.

E.A. Falco, et al., "Studies on Condensed Pyrimidine Systems. X. Some 1,3-Oxazolo (5,4-D)Pyrimidines", J. Am. Chem. Soc., vol. 74, Oct. 5, 1952, pp. 4897-4902, XP-002336123.

Database Crossfire Beilstein, Beilstein Institut zur Foerderung der Wissenschaften, Frankfurt am Main, DE; XP-002336606, Database Accession No. 552904, Abstract Only.

U.S. Appl. No. 11/181,985, filed Jul. 15, 2005, Takahashi, et al.

N. Whittaker, "A New Synthesis and the Chemical Properties of 5-Aminopyrimidine", J. Chem. Soc., 1951, pp. 1565-1570.

(Continued)

*Primary Examiner*—James O Wilson
*Assistant Examiner*—Erich A Leeser
(74) *Attorney, Agent, or Firm*—Oblon, Spivak, McClelland, Maier & Neustadt, P.C.

(57) ABSTRACT

The present invention provides a production method of 5-aminopyrimidine compound represented by the formula (5) by reacting a glycine compound represented by the formula (1) with t-butoxybisdimethylaminomethane, dimethylformamidedimethylacetal or dimethylformamidediethylacetal to produce a dialkylaminomethylene compound represented by the formula (2), reacting the compound of formula (2) in the presence of an acid to produce a hydroxymethylene compound represented by the formula (3), and reacting the compound of formula (3) with an amidine compound represented by the formula (4) or a salt thereof.

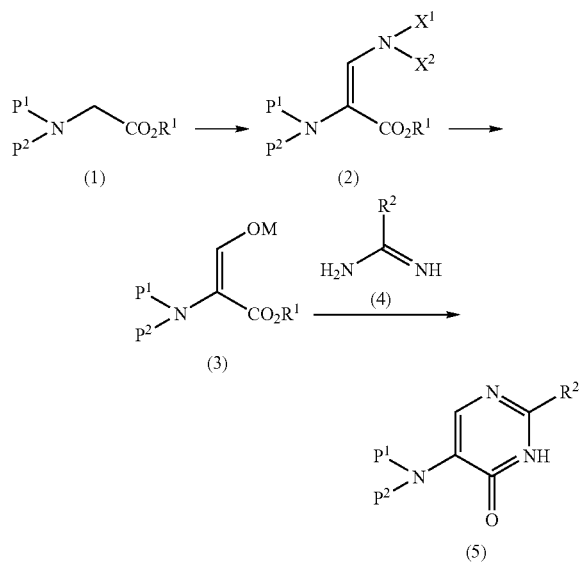

16 Claims, No Drawings

OTHER PUBLICATIONS

K. Yoshida, et al., "Reaction of N-Substituted Cyclic Amines With 2,4-Dichloroquinazoline, 2,4-Dichloropyrimidine, and Its 5-Methyl Derivative", J. Chem. Soc., 1 (7), pp. 919-922, 1992.

D. Montebugnoli, et al., "Regioselective 4-Amino-De-Chlorination of Trichloro-and Dichloro-Pyrimidines With N-Sodium Carbamates", Tetrahedron, 58, 2002, pp. 2147-2153.

M.P. Nemeryuk, et al., "Transformations of Substituted 5-Aminopyrimidines Under Conditions of the Diazotization", Collect. Czech Chem. Comm., vol. 51, No. 11, pp. 215-233, 1986.

L. Benati, et al., "Reaction of Diphenyl Disulfide With Alkynes Promoted by Di-Tert-Butyl and Dibenzoyl Peroxide: A Useful Synthetic Route to 3- (and 2,3-) Substituted Benzo[B]Thiophenes", J. Chem. Soc. Perk. Trans., 1, (7), 1992, pp. 1659-1664.

* cited by examiner

5-PROTECTED AMINOPYRIMIDINE COMPOUND, PRODUCTION METHOD THEREOF AND INTERMEDIATE THEREFOR

CROSS-REFERENCE TO RELATED APPLICATIONS

The present application claims priority to Japanese Application No. JP 2004-77265 filed on Mar. 17, 2004, which is hereby incorporated by reference in its entirety.

BACKGROUND OF THE INVENTION

1. Field of the Invention

The present invention provides a 5-protected aminopyrimidine compound, which is used as an intermediate for various compounds having a pharmacological activity, a production method thereof and an intermediate therefor.

2. Discussion of the Background

A 5-protected aminopyrimidine compound serves as an intermediate for the synthesis of various compounds having a pharmacological activity. These compounds include anticancer agents, NK1 antagonists, elastase inhibitors and the like (U.S. Pat. No. 6,380,206 and WO02/42280).

A method for introducing an amino group into the 5-position of pyrimidine has been known. This known method consists of introducing a nitro group into uracil, and then reducing the same (J. Chem. Soc., 1565-1570, 1951).

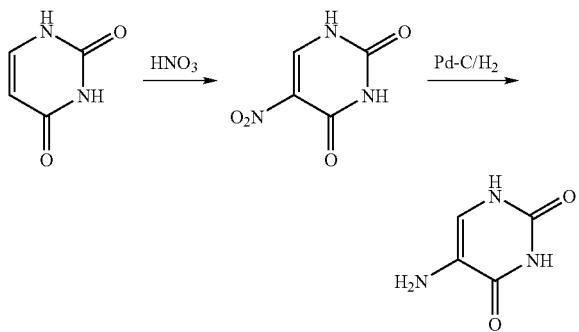

However, the volatility of nitro compounds has lead to a general reticence for use in an industrial production method. In addition, since uracil derivatives have a carbonyl group at both the 2-position and the 4-position, position selective introduction of a substituent into the 2-position or the 4-position is difficult (J. Chem. Soc. Perk. Trans. 1, (7), 919-922, 1992, EP647639A and Tetrahedron, 58 (11) 2147-2153, 2002).

A method of producing an aminopyrimidine compound by using a compound other than uracil as a starting material is known. In this known method, glycine ethyl ester is reacted with ethyl formate and sodium methoxide to produce an ethyl-α-formyl-formyl glycinate sodium salt, which is reacted with an acid addition salt of amidine in methanol to result in formylaminopyrimidine (Collect. Czech Chem. Comm., 51(1), 215-233, 1986).

As a different production method, the production method shown in the following reaction scheme has been reported (J. Chem. Soc. Perk. Trans. 1, (7), 1659-1664, 1988):

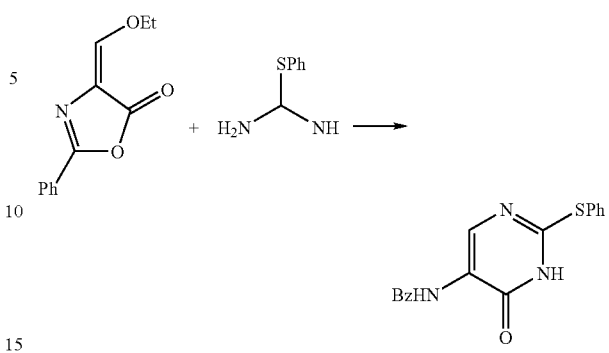

wherein Ph is a phenyl group, Et is an ethyl group, Bz is a benzyl group.

However, the production yields resulting from this method are often unsatisfactory. Moreover, when an amino group at the 5-position of an aminopyrimidine compound is protected with an aliphatic acyl group, deprotection can be conducted under comparatively mild conditions, but a compound having the 2-position (e.g., 2-phenyl-4-ethoxymethylene-azlactone, which is a starting material to be used for this reaction) as an aliphatic group can be obtained only in a comparatively low yield (WO03/106434).

Accordingly, there remains a critical demand for a method of preparing intermediates for anticancer agents, NK1 antagonists, elastase inhibitors in which the process comprises efficient production of a 5-protected aminopyrimidine compound represented by (5), as well as a method that enables the preparation of the desired intermediate in high yield and high purity.

SUMMARY OF THE INVENTION

It is an object of the present invention to provide a method of preparing intermediates for anticancer agents, NK1 antagonists, elastase inhibitors in which the process comprises efficient production of a 5-protected aminopyrimidine compound represented by (5), as well as a method that enables the preparation of the desired intermediate in high yield and high purity.

That is, the present invention provides the following.

[1] A method of making a 5-protected aminopyrimidine compound of formula (5) or salt thereof:

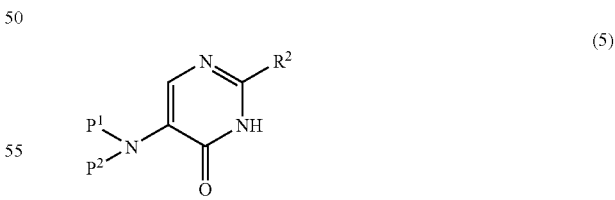

wherein $P^1$ is a hydrogen atom or a benzyl group, $P^2$ is a urethane type protecting group or an acyl type protecting group when $P^1$ is a hydrogen atom, or a benzyl group when $P^1$ is a benzyl group, or $P^1$ and $P^2$ are linked to show a phthaloyl group, and $R^2$ is an alkyl group optionally having substituents, an aryl group optionally having substituents, an aralkyl group optionally having substituents, or a group represented by a formula selected from the group consisting of formula (a), the formula (b), and formula (c):

—O—R⁴ (a)

—S—R⁴ (b)

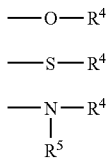 (c)

wherein $R^4$ is an alkyl group optionally having substituents, an aryl group optionally having substituents or an aralkyl group optionally having substituents, $R^5$ is a hydrogen atom, an alkyl group optionally having substituents, an aryl group optionally having substituents or an aralkyl group optionally having substituents, wherein said method comprises (i) reacting a glycine compound of formula (1):

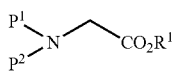 (1)

wherein $R^1$ is an alkyl group and $P^1$ and $P^2$ are as defined above, with a compound selected from the group consisting of t-butoxybisdimethylaminomethane, dimethylformamidedimethylacetal, and dimethylformamidediethylacetal to produce a dialkylaminomethylene compound of formula (2):

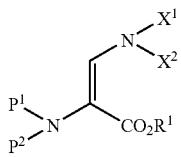 (2)

wherein $P^1$, $P^2$ and $R^1$ are as defined above, $X^1$ and $X^2$ are each independently a methyl group or an ethyl group;

(ii) reacting said dialkylaminomethylene compound of formula (2) in the presence of an acid to produce a hydroxymethylene compound of formula (3):

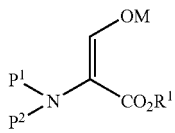 (3)

wherein $P^1$, $P^2$ and $R^1$ are as defined above and M is a hydrogen atom or an alkali metal; and (iii) reacting said hydroxymethylene compound of formula (3) with an amidine compound of formula (4):

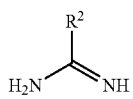 (4)

wherein $R^2$ is as defined above, or a salt thereof.

[2] The production method of [1], wherein $R^1$ is a methyl group or an ethyl group and M is a hydrogen atom, sodium, potassium or lithium.

[3] A hydroxymethylene compound of formula (3-a) or a salt thereof:

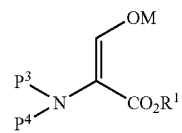 (3-a)

wherein $R^1$ is an alkyl group, $P^3$ is a hydrogen atom or a benzyl group, $P^4$ is a urethane type protecting group when $P^3$ is a hydrogen atom, or a benzyl group when $P^3$ is a benzyl group, or $P^3$ and $P^4$ are linked to show a phthaloyl group, M is a hydrogen atom or an alkali metal.

[4] The compound of [3], wherein $R^1$ is a methyl group or an ethyl group and M is a hydrogen atom, sodium, potassium or lithium.

[5] The compound of [3], wherein the compound of formula (3-a) is methyl-2-benzyloxycarbonylamino-3-hydroxymethylene-glycinate or a alkali metal salt thereof.

[6] A 5-protected aminopyrimidine compound represented by the formula (5-a) or a salt thereof:

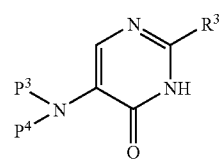 (5-a)

wherein $P^3$ is a hydrogen atom or a benzyl group, $P^4$ is a urethane type protecting group when $P^3$ is a hydrogen atom, or a benzyl group when $P^3$ is a benzyl group, or $P^3$ and $P^4$ are linked to show a phthaloyl group, and $R^3$ is a group of formula (a) or formula (b):

—O—R⁴ (a)

—S—R⁴ (b)

wherein $R^4$ is an alkyl group optionally having substituents, an aryl group optionally having substituents or an aralkyl group optionally having substituents.

[7] The compound of [6], wherein the compound represented by the formula (5-a) is 2-methoxy-6-oxo-5-benzyloxycarbonylamino-1,6-dihydropyrimidine, 2-S-methyl-6-oxo-5-benzyloxycarbonylamino-1,6-dihydropyrimidine or 2-phenyl-6-oxo-5-benzyloxycarbonylamino-1,6-dihydropyrimidine.

The aminopyrimidine compound represented by the formula (5) in the present invention can, in an aminopyrimidine compound represented by the following formula (5-b) and (5-c) for example, be selectively aminated at the 2-position (see J. Heterocyclic Chem., 19(5), 1117-1124, 1982 and J. Chem. Soc. Perk. Trans. 1 (7), 1659-1664, 1988), and can also be selectively chlorinated at the 4-position (see Research Disclosure, 452068, 10, Dec. 2001 and Ger. Offen., 3423622, 1986). Therefore, various substituents can be introduced into the 2-position and the 4-position of the aminopyrimidine compound to give various compounds.

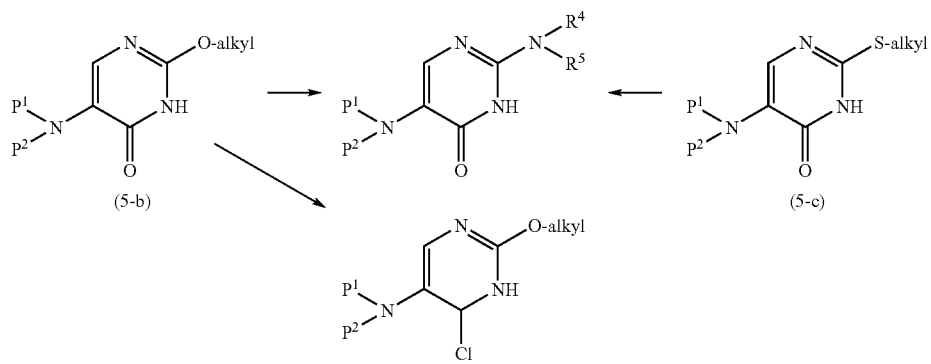

wherein $P^1$, $P^2$, $R^4$ and $R^5$ are as defined above and alkyl means an alkyl group.

The compound of the formula (3-a) of the present invention is a superior intermediate for the production of a useful compound of the formula (5).

It is another object of the present invention to provide novel methods for preparing anticancer agents, NK1 antagonists, elastase inhibitors, by using the compound of formula (5) or a salt thereof produced by the present method.

The above objects highlight certain aspects of the invention. Additional objects, aspects and embodiments of the invention are found in the following detailed description of the invention.

DETAILED DESCRIPTION OF THE INVENTION

Unless specifically defined, all technical and scientific terms used herein have the same meaning as commonly understood by a skilled artisan in enzymology, biochemistry, cellular biology, molecular biology, and the medical sciences.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will control. Further, the materials, methods, and examples are illustrative only and are not intended to be limiting, unless otherwise specified.

According to the finding of the present inventors, however, in the method described in the article published in Collect. Czech Chem. Comm., referenced above, when an amino group of a glycine compound represented by (1) is protected by a benzyloxycarbonyl group or a phthaloyl group, a reaction to introduce into a hydroxymethylene compound represented by (3) is conducted in the presence of a strong base, thus causing decomposition of these protecting groups. As such, the desired product becomes unattainable. In addition, when protected with a t-butoxycarbonyl group, an acyl group and the like, the yield was not necessarily satisfactory (see Comparative Example 1 below).

Therefore, in the present invention, the inventors sought to provide an efficient production method of a 5-aminopyrimidine compound represented by the formula (5).

The present inventors have conducted intensive studies in an attempt to satisfy this goal and found that a 5-aminopyrimidine compound represented by the formula (5) can be efficiently obtained by reacting a glycine compound represented by the formula (1) as the starting material with t-butoxybisdimethylaminomethane, dimethylformamidedimethylacetal or dimethylformamidediethylacetal to produce a compound represented by the formula (2). The compound of formula (2) is then reacted in the presence of an acid to lead to a hydroxymethylene compound represented by the formula (3) or a salt thereof. Subsequently, the compound of formula (30) is reacted with an amidine compound represented by the formula (4) or a salt thereof to provide the desired compound of formula (5) or salt thereof.

In the description of the present invention, the following definitions are used for the various symbols used herein:

In the formulas of the present invention, the alkyl group for $R^1$ is preferably alkyl having 1 to 4 carbon atoms, more preferably a methyl group or an ethyl group, and particularly preferably a methyl group.

In the formulas of the present invention, $P^1$ is a hydrogen atom or a benzyl group. When $P^1$ is a hydrogen atom, $P^2$ is a urethane type protecting group or an acyl type protecting group. When $P^1$ is a benzyl group, $P^2$ is a benzyl group. Alternatively, $P^1$ and $P^2$ are linked to show a phthaloyl group.

The urethane type protecting group can be represented by $P^5$—O—CO—. Here, $P^5$ is an alkyl group optionally having substituents or an aralkyl group optionally having substituents. The alkyl group, the aralkyl group and the substituents are the same as those shown below. As preferable urethane type protecting group, a benzyloxycarbonyl group, a t-butoxycarbonyl group, a methoxyoxycarbonyl group and the like can be mentioned.

The acyl type protecting group can be represented by $P^6$—CO—. Here, $P^6$ is an alkyl group optionally having substituents or an aralkyl group optionally having substituents. The alkyl group, the aralkyl group and the substituents are the same as those shown below. As preferable acyl type protecting group, an acetyl group, a propionyl group, a benzoyl group and the like can be mentioned.

In the formulae of the present invention, $R^2$ is an alkyl group optionally having substituents, an aryl group optionally having substituents, an aralkyl group optionally having substituents or a group represented by the formula (a), (b) or (c):

In formulae (a), (b) and (c), $R^4$ and $R^5$ are each independently an alkyl group optionally having substituents, an aryl group optionally having substituents or an aralkyl group optionally having substituents. Particularly, a group represented by the formula (a) is preferable.

As the "alkyl group" for $R^2$, $R^4$, $R^5$ or alkyl, a linear or branched chain alkyl group preferably having 1 to 20, more preferably 1 to 7, carbon atoms can be mentioned. Specifically, for example, alkyl groups such as a methyl group, an ethyl group, an n-propyl group, an isopropyl group, an n-butyl group, an isobutyl group, a sec-butyl group, a tert-butyl group, a lauryl group and the like can be mentioned. Of these, a methyl group and an ethyl group are preferable.

The alkyl group is optionally substituted by one or more substituents below. As the substituent here, for example, a linear or branched chain alkoxy group (carbon number: 1-6, e.g., methoxy group), a halogen atom (e.g., chlorine atom, fluorine atom and the like), a hydroxyl group and the like can be mentioned.

As the "aryl group" for $R^2$, $R^4$ or $R^5$, an aryl group preferably having 6 to 20, more preferably 6 to 8, carbon atoms can be mentioned. The aryl group is optionally substituted by one or more substituents below. As the substituent here, for example, a nitro group, a linear or branched chain alkoxy group (carbon number: 1-6, e.g., methoxy group), a halogen atom (e.g., chlorine atom, fluorine atom and the like), a linear or branched chain alkyl group (preferable carbon number: 1-4, e.g., methyl group, ethyl group, propyl group and the like), a hydroxyl group and the like can be mentioned. Specific examples of the aryl group optionally having substituents include phenyl group, o-, m- or p-nitrophenyl group, o-, m- or p-methoxyphenyl group, o-, m- or p-chlorophenyl group, o-, m- or p-fluorophenyl group, o-, m- or p-tolyl group and the like can be mentioned. As $R^2$, phenyl group and p-chlorophenyl group are preferable.

The "aralkyl group" for $R^2$, $R^4$ or $R^5$ is an aralkyl group wherein the aryl moiety preferably has 6 to 12, more preferably 6 to 8, carbon atoms, and the alkyl moiety is a linear or branched chain alkyl group preferably having 1 to 6, more preferably 1 to 3, carbon atoms. As the aralkyl group, a benzyl group is preferable.

The alkyl group is optionally substituted by one or more substituents below. As the substituent here, for example, a nitro group, a linear or branched chain alkoxy group (carbon number: 1-6, e.g., methoxy group), a halogen atom (e.g., chlorine atom, fluorine atom and the like), a hydroxyl group and the like can be mentioned.

In the formulae of the present invention, M is a hydrogen atom or an alkali metal, preferably hydrogen, sodium, potassium or lithium, and particularly preferably sodium or potassium.

In the production method of the present invention, a glycine compound represented by the formula (1) is reacted with t-butoxybisdimethylaminomethane, dimethylformamidedimethylacetal or dimethylformamidediethylacetal to give a dialkylaminomethylene compound represented by the formula (2) (Heterocyclic Chem., 36, 225, 1999).

The solvent to be used for the reaction is not limiting so as long as it does not inhibit the reaction and, for example, toluene, acetonitrile, butyl acetate and the like can be mentioned. One or more kinds of these may be used in combination. Particularly, toluene is preferable. The amount of the solvent to be used is generally 2-50 parts by weight, preferably 5-20 parts by weight, per 1 part by weight of the compound of the formula (1).

The amount of t-butoxybisdimethylaminomethane, dimethylformamidedimethylacetal or dimethylformamidediethylacetal to be used is preferably 1-3 mol, more preferably 1-2 mol, per 1 mol of the glycine compound of the formula (1).

The reaction temperature for the present invention ranges from 40° C. to the refluxing temperature, preferably 60-110° C. The reaction completes within the above-mentioned temperature range generally for 0.5-24 hr, preferably 1-8 hr.

After the completion of the reaction, the reaction solution can generally be used as it is for the next reaction (i.e., recycled). Where necessary, the compound of the formula (2) can be isolated from the reaction solution and used for the next reaction. In this case, the isolation method is not particularly limited, and various methods known to those of ordinary skill in the art, such as extraction, crystallization, chromatography and the like, can be used.

Then, a dialkylaminomethylene compound represented by the formula (2) is reacted in the presence of an acid resulting in a hydroxymethylene compound represented by the formula (3). As the acid to be used here, hydrochloric acid, sulfuric acid and the like can be preferably mentioned. When a monovalent acid is used, the amount of the acid to be used is not less than 1 mol, generally 1-20 mol, preferably 2-5 mol, per 1 mol of the compound of the formula (2). The acid is preferably used in the form of an aqueous solution. In this case, the concentration of the aqueous acid solution is 0.01N to 6N, preferably 0.1N to 3N.

As the reaction solvent, a two-layer system of water and a nonaqueous organic solvent is preferably employed. As the nonaqueous organic solvent, ethyl acetate, propyl acetate, butyl acetate, MTBE, diethyl ether, toluene and dichloromethane can be mentioned. The amount of the solvent to be used is generally 2-50 parts by weight, preferably 5-20 parts by weight, per 1 part by weight of the compound of the formula (2).

The reaction temperature is in the range of generally 0-40° C., preferably 5-30° C. This reaction completes in the above-mentioned temperature range generally for 0.5-24 hr, preferably 1-5 hr.

After the completion of the reaction, a base is added to the reaction solution for neutralization. In the neutralizing step, the compound of the formula (3) (hereinafter to be also referred to as compound (3)) is converted to an alkali metal salt, or a free embodiment wherein, in the formula (3), M is a hydrogen atom. When the amidine compound (4) to be used in the next step is an acidic salt, compound (3) is preferably converted to an alkali metal salt. When compound (3), which is a free embodiment, is used here, the amidine compound (4) needs to be neutralized by the addition of a base in the next step. When the amidine compound (4) to be used in the next step is a free base, compound (3) of a free embodiment is preferably used.

As the base to be used for neutralization, sodium methoxide, sodium ethoxide, potassium methoxide, potassium butoxide, sodium hydroxide, potassium hydroxide, lithium hydroxide, sodium hydride, potassium hydride and the like can be mentioned. Particularly, sodium methoxide, sodium hydroxide and potassium tert-butoxide are preferable.

The amount of the base to be used is not particularly limiting, and is generally 0.8-3 mol, preferably 1-1.5 mol, per 1 mol of compound (3).

After the neutralization, the reaction solution can be generally used for the next reaction cycle. Where necessary, a solution may be concentrated or the solvent may be substituted. When a hydroxymethylene compound represented by the formula (3) is isolated from the reaction solution, the method thereof is not particularly limited, and a method known to those of ordinary skill in the art can be employed. For example, a solvent may be evaporated, the residue is washed with diethyl ether and the like, filtered and dried to give compound (3).

The compound of the formula (3) is preferably a compound represented by the aforementioned formula (3-a), more preferably methyl-2-benzyloxycarbonylamino-3-hydroxymethylene-glycinate or an alkali metal salt thereof.

Then, a hydroxymethylene compound represented by the formula (3) is reacted with an amidine compound represented by the formula (4) to lead to a 5-aminopyrimidine compound represented by the formula (5).

The solvent to be used for the reaction is not limited as long as it does not inhibit the reaction and, for example, water, methanol, ethanol, isopropanol, acetates (e.g., ethyl acetate, isopropyl acetate, isobutyl acetate, n-butyl acetate and the like), acetonitrile, tetrahydrofuran (THF), acetone, N,N-dimethylformamide and the like can be mentioned. One or more kinds of these may be used in combination. Particularly, water-soluble organic solvents such as methanol, acetonitrile, acetone and the like are more preferable. Of these, methanol, ethanol and acetonitrile are preferable. The amount of the solvent to be used is generally 3-50 parts by weight, preferably 5-20 parts by weight, per 1 part by weight of the compound of the formula (4).

In the reaction, the amount of the amidine compound represented by the formula (4) to be used is preferably 0.8-3.0 mol, more preferably 1-1.5 mol, per 1 mol of a hydroxymethylene compound represented by the formula (3).

The reaction temperature is generally 10° C.—the refluxing temperature of the solvent to be used, preferably 20-80° C. This reaction completes within the above-mentioned temperature range for generally 1-24 hr, preferably 2-8 hr.

After the completion of the reaction, it is possible to employ a method of isolating the obtained compound of the formula (5), which is not particularly limited and various methods known to those of ordinary skill in the art can be used. Generally, since a compound of the formula (5) is crystallized during the reaction, for example, a compound of the formula (5) can be isolated by, after the completion of the reaction, filtering the crystal where necessary, washing the crystal and drying the separated crystal. In addition, before filtration of the crystal, the reaction solution may be concentrated, cooled, a poor solvent may be added and the like to further perform crystallization.

The compound of the formula (5) is preferably a compound represented by the formula (5-a) above. More preferably, the compound of formula (5) is selected from 2-methoxy-6-oxo-5-benzyloxycarbonylamino-1,6-dihydropyrimidine, 2-S-methyl-6-oxo-5-benzyloxycarbonylamino-1,6-dihydropyrimidine, and 2-phenyl-6-oxo-5-benzyloxycarbonylamino-1,6-dihydropyrimidine.

According to the present invention, the aforementioned 5-aminopyrimidine compound represented by the formula (5) is an effective intermediate for various compounds having a pharmacological activity can be produced efficiently.

In another embodiment, the present invention provides methods for preparing anticancer agents, NK1 antagonists, or elastase inhibitors, by converting a 5-protected aminopyrimidine compound of formula (5):

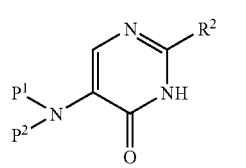

(5)

or a salt thereof, produced by the present method to such anticancer agents, NK1 antagonists, or elastase inhibitors.

The 5-protected aminopyrimidine compound of formula (5) or salt thereof produced by the present method may be converted to such anticancer agents, NK1 antagonists, or elastase inhibitors by the methods described in, e.g., U.S. Pat. No. 6,380,206 and WO00/242280, which are incorporated herein in their entireties. The 5-protected aminopyrimidine compound of formula (5) or salt thereof produced by the present method may also be selectively aminated at the 2-position (see J. Heterocyclic Chem., 19(5), 1117-1124, 1982 and J. Chem. Soc. Perk. Trans. 1 (7), 1659-1659, 1988, both of which are incorporated herein by reference in their entireties), or can be selectively chlorinated at the 4-position (see Research Disclosure, 452068, Dec. 10, 2001 and Ger. Offen., 3423622, 1986, both of which are incorporated herein by reference in their entireties).

The above written description of the invention provides a manner and process of making and using it such that any person skilled in this art is enabled to make and use the same, this enablement being provided in particular for the subject matter of the appended claims, which make up a part of the original description.

As used above, the phrases "selected from the group consisting of," "chosen from," and the like include mixtures of the specified materials.

Where a numerical limit or range is stated herein, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

Having generally described this invention, a further understanding can be obtained by reference to certain specific examples, which are provided herein for purposes of illustration only, and are not intended to be limiting unless otherwise specified.

EXAMPLES

Example 1

Toluene (15 ml) was added to methyl-N-benzyloxycarbonyl-glycinate (1.50 g, 6.7 mmol) and tert-butoxybisdimethylaminomethane (1.84 ml, 8.8 mmol) and the mixture was stirred overnight at 70° C. The mixture was washed with water and saturated brine at room temperature. The resultant organic layer was concentrated under reduced pressure to produce methyl-2-benzyloxycarbonylamino-3-dimethylaminoglycinate (1.83 g, 6.6 mmol).

$^1$H-NMR (CDCl$_3$) δ ppm: 3.01 (6H,s), 3.66 (3H,s), 5.15 (2H,s), 5.57 (1H,s), 7.26-7.37 (6H,m)

MS (ESI) m/z [MH]$^+$ 279.2

Example 2

MTBE (20 ml) and 1N hydrochloric acid (15 ml) were added to methyl-2-benzyloxycarbonylamino-3-dimethylamino glycinate (2.38 g, 8.55 mmol) in an ice bath and the mixture was stirred at room temperature for 2 hr. Subsequently, the mixture was separated and the organic layer was washed with saturated brine, followed by drop-wise addition of a solution (1.50 g, 8.00 mmol) of 28% sodium methoxide in methanol. Thereafter, the solvent was evaporated and the residue was washed by adding diethyl ether. The precipitate was filtered and vacuum dried to give methyl-2-benzyloxycarbonylamino-3-hydroxymethylene-glycinate sodium salt (2.12 g, 7.76 mmol).

$^1$H-NMR (DMSO-$d_6$) δ ppm: 3.40 (3H,s), 4.96 (2H,s), 6.83 (1H,s), 7.32-7.37 (5H,m), 8.75 (1H,s)

Example 3

Toluene (10 ml) was added to N-benzyloxycarbonyl-glycine methyl ester (1.50 g, 6.73 mmol) and tert-butoxybisdimethylaminomethane (1.83 ml, 8.91 mmol) and the mixture was stirred overnight at 70° C. The mixture was washed with saturated brine and concentrated under reduced pressure. MTBE (20 ml) and 1N hydrochloric acid (15 ml) were added to the residue in an ice bath and the mixture was stirred at room temperature for 2 hr. Thereafter, the mixture was separated and the organic layer was washed with saturated brine. A solution (1.23 g, 6.39 mmol) of 28% sodium methoxide in methanol was added drop-wise and the mixture was concentrated under reduced pressure. The solvent was substituted by acetonitrile and O-methylisourea hydrochloride (0.72 g, 6.50 mmol) was added. The mixture was stirred overnight at 70° C. and concentrated. Water (5 ml) was added and the mixture was stirred for 1 hr. The precipitate was collected by filtration and vacuum dried to give 2-methoxy-6-oxo-5-benzyloxycarbonylamino-1,6-dihydropyrimidine (1.43 g, 5.20 mmol).

$^1$H-NMR (DMSO-$d_6$) δ ppm: 3.85 (3H,s), 5.12 (2H,s), 7.31-7.41 (5H,m), 7.95 (1H,s), 8.45 (1H,s), 12.61 (1H,brs)

MS (ESI) m/z [MH]$^+$ 275.6

Example 4

Toluene (10 ml) was added to methyl-N-benzyloxycarbonyl-glycinate (1.50 g, 6.73 mmol) and tert-butoxybisdimethylaminomethane (1.83 ml, 8.91 mmol) and the mixture was stirred overnight at 70° C. The mixture was then washed with saturated brine and concentrated under reduced pressure. MTBE (20 ml) and 1N hydrochloric acid (15 ml) were added to the residue in an ice bath and the mixture was stirred at room temperature for 2 hr. Thereafter, the mixture was separated and the organic layer was washed with saturated brine. A solution (1.23 g, 6.39 mmol) of 28% sodium methoxide in methanol was added dropwise and the mixture was concentrated under reduced pressure. Acetonitrile was added and O-methylisourea hydrochloride (0.72 g, 6.50 mmol) was added. The mixture was stirred overnight at 70° C. and concentrated. Water (5 ml) was added and the mixture was stirred for 1 hr. The precipitate was collected by filtration and vacuum dried to give 2-methoxy-6-oxo-5-benzyloxycarbonylamino-1,6-dihydropyrimidine (1.43 g, 5.20 mmol). The property values were the same as in Example 3.

Example 5

In the same manner as in Example 3, 2-S-methyl-6-oxo-5-benzyloxycarbonylamino-1,6-dihydropyrimidine (0.22 g, 0.76 mmol) was obtained from methyl-2-benzyloxycarbonylamino-3-hydroxymethylene-glycinate sodium salt (0.30 g, 1.10 mmol) and S-methylisourea sulfate (0.17 g, 0.58 mmol).

$^1$H-NMR (DMSO-$d_6$) δ ppm: 2.48 (3H,s), 5.13 (2H,s), 7.31-7.43 (5H,m), 8.17 (1H,s), 8.59 (1H,s), 13.0 (1H,brs)

MS (ESI) m/z [MH]$^+$ 292.2

Example 6

In the same manner as in Example 4, 2-phenyl-6-oxo-5-benzyloxycarbonylamino-1,6-dihydropyrimidine (0.19 g, 0.61 mmol) was obtained using methyl-N-benzyloxycarbonyl-glycinate (0.18 g, 0.81 mmol) and benzamidine hydrochloride (0.13 g, 0.81 mmol).

$^1$H-NMR (DMSO-$d_6$) δ ppm: 5.18 (2H,s), 7.39-7.53 (8H, m), 8.08 (2H,s), 8.46 (1H,s), 8.80 (1H,s), 13.04 (1H,brs)

MS (ESI) m/z [MH]$^+$ 321.6

Comparative Example 1

Under a nitrogen atmosphere, MTBE (3 ml) was added to 60% sodium hydride (0.10 g). Methyl-N-tert-butoxycarbonyl-glycinate (0.39 g, 2.05 mmol) and methyl formate (0.31 g, 5.13 mmol) were dissolved in MTBE (2 ml) in an ice bath and the solution was added dropwise over 1 hr. After overnight stirring at normal temperature, the precipitate was collected by filtration and the crystal and O-methylisourea hydrochloride (0.22 g, 2.05 mmol) were stirred overnight at 40° C. in methanol. The reaction mixture was analyzed by HPLC. As a result, 2-methoxy-6-oxo-5-tert-butoxycarbonylamino-1,6-dihydropyrimidine (0.21 g, 0.88 mmol, yield 43%) was contained.

Numerous modifications and variations on the present invention are possible in light of the above teachings. It is, therefore, to be understood that within the scope of the accompanying claims, the invention may be practiced otherwise than as specifically described herein.

The invention claimed is:

1. A method of making a 5-protected aminopyrimidine compound represented by (5) or salt thereof:

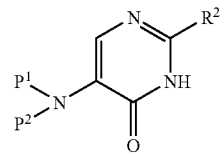

(5)

wherein $P^1$ is a hydrogen atom or a benzyl group, $P^2$ is a urethane type protecting group or an acyl type protecting group when $P^1$ is a hydrogen atom, or a benzyl group when $P^1$ is a benzyl group, or $P^1$ and $P^2$ are linked to show a phthaloyl group, and $R^2$ is an alkyl group optionally having substituents, an aryl group optionally having substituents, an aralkyl group optionally having substituents, or a group represented by a formula selected from the group consisting of formula (a), the formula (b), and formula (c):

—O—R$^4$                                                  (a)

—S—R$^4$                                                 (b)

—N—R$^4$                                              (c)
 |
R$^5$ wherein $R^4$ is an alkyl group optionally having substituents, an aryl group optionally having substituents or an aralkyl group optionally having substituents, $R^5$ is a hydrogen atom, an alkyl group optionally having substituents, an aryl group optionally having substituents or an aralkyl group optionally having substituents, wherein said method comprises (i) reacting a glycine compound of formula (1):

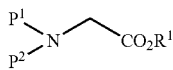
(1)

wherein $R^1$ is an alkyl group and $P^1$ and $P^2$ are as defined above, with a compound selected from the group consisting of t-butoxybisdimethylaminomethane, dimethylformamidedimethylacetal, and dimethylformamidediethylacetal to produce a dialkylaminomethylene compound of formula (2):

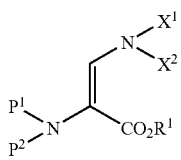
(2)

wherein $P^1$, $P^2$ and $R^1$ are as defined above, $X^1$ and $X^2$ are each independently a methyl group or an ethyl group;

(ii) reacting said dialkylaminomethylene compound of formula (2) in the presence of an acid to produce a hydroxymethylene compound of formula (3):

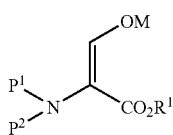
(3)

wherein $P^1$, $P^2$ and $R^1$ are as defined above and M is a hydrogen atom or an alkali metal; and (iii) reacting said hydroxymethylene compound of formula (3) with an amidine compound of formula (4):

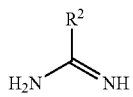
(4)

wherein $R^2$ is as defined above, or a salt thereof, to produce the 5-protected aminopyrimidine compound represented by (5) or salt thereof.

2. The method of claim 1, wherein $R^1$ is a methyl group or an ethyl group and M is a hydrogen atom, sodium, potassium or lithium.

3. The method of claim 1, wherein (i) is at a temperature ranging from 40° C. to the refluxing temperature for a reaction time ranging from 0.5 to 24 hr.

4. The method of claim 1, wherein (i) is conducted in a solvent selected from the group consisting of toluene, acetonitrile, and butyl acetate.

5. The method of claim 1, wherein said acid in (ii) is hydrochloric acid or sulfuric acid.

6. The method of claim 1, wherein said acid in (ii) is present in an amount of not less than 1 mol per 1 mol of compound of formula (2).

7. The method of claim 1, wherein (ii) is conducted in a two-layer system comprising water and a nonaqueous organic solvent.

8. The method of claim 7, wherein said nonaqueous organic solvent is selected from the group consisting of ethyl acetate, propyl acetate, butyl acetate, MTBE, diethyl ether, toluene and dichloromethane.

9. The method of claim 1, wherein (ii) is at a temperature ranging from 0 to 40° C. for a reaction time ranging from 0.5 to 24 hr.

10. The method of claim 1, further comprising, following (ii), adding a base.

11. The method of claim 10, wherein said base is selected from the group consisting of sodium methoxide, sodium ethoxide, potassium methoxide, potassium butoxide, sodium hydroxide, potassium hydroxide, lithium hydroxide, sodium hydride, and potassium hydride.

12. The method of claim 1, wherein (iii) is conducted in a solvent selected from the group consisting of water, methanol, ethanol, isopropanol, an acetate, acetonitrile, tetrahydrofuran, acetone, and N,N-dimethylformamide.

13. The method of claim 1, wherein the amount of the amidine compound represented by the formula (4) to be used is preferably 0.8-3.0 mol per 1 mol of a hydroxymethylene compound of formula (3).

14. The method of claim 1, wherein (iii) is at a temperature ranging from 10° C.—the refluxing temperature of the solvent to be used for a reaction time ranging from 1 to 24 hr.

15. The method of claim 1, further comprising:

(iv) isolating the obtained compound of the formula (5).

16. In a method for producing a anticancer agents, NK1 antagonists, or elastase inhibitors, which comprises converting 5-protected aminopyrimidine compound of formula (5) or salt thereof to said anticancer agents, NK1 antagonists, elastase inhibitors, wherein the improvement comprises preparing said 5-protected aminopyrimidine compound of formula (5) or salt thereof by the method of claim 1.

* * * * *